United States Patent [19]

Griffith et al.

[11] Patent Number: 5,364,881
[45] Date of Patent: Nov. 15, 1994

[54] S-ALKYL-ISOTHIOUREIDO-AMINO ACIDS AND USE THEREOF

[75] Inventors: Owen W. Griffith, Milwaukee; Krishnaswamy Narayanan, Wauwatosa, both of Wis.

[73] Assignee: The Medical College of Wisconsin Research Foundation, Inc., Milwaukee, Wis.

[21] Appl. No.: 152,010

[22] Filed: Nov. 15, 1993

[51] Int. Cl.$^5$ .................. A61K 31/215; C07C 335/32
[52] U.S. Cl. .......................... 514/508; 558/5
[58] Field of Search ........................ 558/5; 514/508

[56] References Cited

U.S. PATENT DOCUMENTS

| | | | |
|---|---|---|---|
| 5,216,025 | 6/1993 | Gross et al. | 514/565 |
| 5,281,627 | 1/1994 | Griffith | 514/565 |
| 5,296,466 | 3/1994 | Kilbourn et al. | 514/6 |

FOREIGN PATENT DOCUMENTS 1096894  1/1961  Germany .
1804894  8/1969  Germany .

OTHER PUBLICATIONS

Adnot, S., et al, Chem. Abstr. 119:46606f (1992).
Hishikawa, K., Chem. Abstr. 117:5022c (1992).
Griffith, O. W., et al, poster titled "Inhibitions of Nitric Oxide Synthase: Structural Constraints on Binding and Mechanism of Action" presented at the 3rd International Meeting on the Biology of Nitric Oxide, Cologne, Germany, Oct. 1993.
Bodanszky, M., et al, The Practice of Peptide Synthesis, Springer-Verlang, New York, 1984, pp. 48, 49, 153, 154.
Feldman, P. L., Tetrahedron Lett., 32, 875–878, 1991.
Rees, D. D., et al, Br. J. Pharmacol., 96, 418–424 (1989).
Gray, G. A., et al, Br. J. Pharmacol., 103, 1218–1224 (May 1991).
Aisaka, K., et al, Biochem. Biophys. Res. Commun. 163, No. 2, 710–717 (Sep. 15, 1989).
Jolou-Schaeffer, G., et al, Am. J. Physiol. 259, H1038–H1043, Oct. 1990.

*Primary Examiner*—Mary C. Lee
*Assistant Examiner*—M. G. Ambrose

[57] ABSTRACT

Inhibitors of nitric oxide formation from arginine useful for treating hypotension, inflammation, stroke and to restore vascular contractile sensitivity to the effects of $\alpha_1$-adrenergic agonists are physiologically active compounds including $N^\delta$-substituted ornithine or $N^\epsilon$-substituted lysine moieties or monoalkyl carbon-substituted $N^\delta$-substituted ornithine or $N^\epsilon$-substituted lysine moieties, having the formula

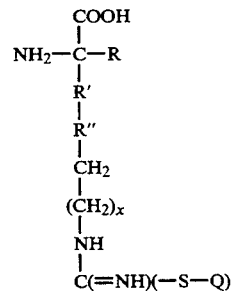

wherein R is $(CH_2)_y CH_3$ or H, R' is $CH_2$ or $C(H)(CH_2)_y CH_3$, and R" is $CH_2$ or $C(H)(CH_2)_y CH_3$, with y ranging from 0 to 5, and x is 0 or 1 and wherein none or only one of R, R' and R" provides an alkyl substituent on ornithine or lysine moiety, and wherein Q is alkyl having 1 to 5 carbon atoms, and physiologically acceptable acid addition salts thereof.

17 Claims, 5 Drawing Sheets

S-ALKYL-ISOTHIOUREIDO-AMINO ACIDS AND USE THEREOF

TECHNICAL FIELD

The invention is directed to novel inhibitors of biological nitric oxide formation.

BACKGROUND OF THE INVENTION

For several decades nitroglycerin has been administered to humans as a vasodilating agent in the treatment of cardiovascular disease. It has been shown that nitroglycerin so administered is converted in the body to nitric oxide which is the pharmacologically active metabolite. Recently, nitric oxide has been shown to be formed enzymatically as a normal metabolite from arginine in vascular endothelium to provide an important component of endothelium-derived relaxing factors (EDRFs) which are currently being intensively studied as participating in regulation of blood flow and vascular resistance. Macrophages have also been shown to produce nitric oxide in the body as a component of their cell killing and/or cytostatic function.

More recently it has been established that the enzyme forming nitric oxide from arginine, i.e., nitric oxide synthase, occurs in at least two distinct forms, namely constitutive forms and an inducible form. The constitutive forms are present in normal endothelial cells, neurons and some other tissues. Formation of nitric oxide by constitutive forms in endothelial cells is thought to play a role in normal blood pressure regulation. The inducible form of nitric oxide synthase has been found to be present in activated macrophages and is induced in endothelial cells and vascular smooth muscle cells, for example, by various cytokines and/or microbial products. It is thought that in sepsis or cytokine-induced shock, overproduction of nitric oxide by the inducible form of nitric oxide synthase plays an important role in the observed life-threatening hypotension. Furthermore, it is thought that overproduction of nitric oxide by the inducible form of nitric oxide synthase is a basis for insensitivity to clinically used pressor agents such as $\alpha_1$-adrenergic agonists in the treatment of septic or cytokine-induced shock patients. Moreover, it is thought that overproduction of nitric oxide by inducible form of nitric oxide synthase is involved in inflammation incident to an immune response.

SUMMARY OF THE INVENTION

It is an object of one embodiment of the invention herein to provide novel arginine or citrulline antagonists which inhibit constitutive form of nitric oxide synthase or inducible form of nitric oxide synthase or both.

The novel compounds herein are physiologically active compounds including $N^\delta$-substituted ornithine or $N^\epsilon$-substituted lysine moieties or monoalkyl carbon-substituted $N^\delta$-substituted ornithine or $N^\epsilon$-substituted lysine moieties, having the formula wherein R is $(CH_2)_y CH_3$ or H, R' is $CH_2$ or $C(H)(CH_2)_y CH_3$, and R" is $CH_2$ or $C(H)(CH_2)_y CH_3$, with y ranging from 0 to 5, and x is 0 or 1 and wherein none or only one of R, R' and R" provides an alkyl substituent on ornithine or lysine moiety, and wherein Q is alkyl having 1 to 5 carbon atoms, and physiologically acceptable acid addition salts thereof.

Preferably Q is methyl.

Preferred compounds are S-methyl-L-thiocitrulline (the above structural formula where R is H, R' is $CH_2$, R" is $CH_2$, x is 0, and Q is $CH_3$) and S-methyl-L-homothiocitrulline (the above structural formula where R is H, R' is $CH_2$, R" is $CH_2$, x is 1 and Q is $CH_3$) and the physiologically acceptable acid addition salts thereof.

The physiologically acceptable acid addition salts include, for example, acetate, hydrochloride, sulfate, phosphate, succinate, citrate and propionate acid addition salts.

The term "physiologically active" refers to L-enantiomer whether pure or in admixture with D-enantiomer. The D-enantiomers are not physiologically active or are much less active than the L-enantiomers. Thus, in the D,L-compounds only the L-enantiomer portion is physiologically active.

Preferably the compounds are pharmaceutically pure, i.e., more than 99% by weight pure (on a water free basis) and contain from 99% to 100% by weight of L-enantiomer (on an L- and D-enantiomer basis).

It is an object of another embodiment herein to provide methods for prophylaxis or treatment of a subject for systemic hypotension or expected systemic hypotension caused by pathological overproduction of nitric oxide from arginine by nitric oxide synthase induced in vascular cells in said subject by a cytokine or by a bacterial endotoxin. One of these methods comprises administering to said subject a therapeutically effective amount of a compound of the invention herein. Another of these methods comprises administering to said subject a conventional amount of at least one $\alpha_1$-adrenergic agonist and an amount of compound of the invention herein effective to restore vascular contractile sensitivity to the effects of said $\alpha_1$-adrenergic agonist.

It is an object of another embodiment herein to suppress an immune response in a subject in need of said suppressing, e.g., where the immune response is part of a pathological inflammatory response. This method comprises administering to a subject in need of said suppressing of an immunosuppressive effective amount, e.g., an inflammation ameliorating amount, of compound of the invention herein.

It is an object of still another embodiment herein to provide a method of prophylaxis or treatment of a subject for a stroke. This method comprises administering to said subject of a therapeutically effective amount, e.g., a neuronal cell protecting amount, of a compound of the invention herein.

The term "subject" is used herein to mean any mammal, including humans, where nitric oxide formation from arginine occurs.

The term "prophylaxis" is used herein to mean to prevent or delay the occurrence of a condition or to ameliorate the symptoms of a condition should it occur compared to where prophylaxis is not carried out.

DETAILED DESCRIPTION

We turn now in more detail to the novel compounds herein.

As indicated above, one group of compounds herein consists of those where none of R, R' and R" provides an alkyl substituent on ornithine or lysine moiety. Where this is the case, the compounds herein are those including ornithine or lysine moieties without monoalkyl carbon-substitution thereon. Ornithine moiety is the case where x equals zero. Lysine moiety is the case where x is 1.

As indicated above, another group of compounds herein consists of those where one of R, R' and R" provides an alkyl substituent on ornithine or lysine moiety. Where this is the case, the compounds herein are those including monoalkyl carbon-substituted ornithine or lysine moieties. Monoalkyl carbon-substituted ornithine moiety is the case where x equals zero. Monoalkyl carbon-substituted lysine moiety is the case where x is 1.

Examples of specific compounds having the structural formula set forth above where none of R, R' and R" provides an alkyl substituent on ornithine or lysine moiety are S-methyl-L-thiocitrulline, S-ethyl-L-thiocitrulline, S-propyl-L-thiocitrulline, S-isopropyl-L-thiocitrulline, S-cyclopropyl-L-thiocitrulline, S-butyl-L-thiocitrulline, S-isobutyl-L-thiocitrulline, S-methylcyclopropyl-L-thiocitrulline, S-pentyl-L-thiocitrulline, S-isopentyl-L-thiocitrulline, S-methyl-L-homothiocitrulline, S-ethyl-L-homothiocitrulline, S-propyl-L-homothiocitrulline, S-isopropyl-L-homothiocitrulline, S-isobutyl-L-homothiocitrulline, S-methylcyclopropyl-L-homothiocitrulline, S-pentyl-L-homothiocitrulline and S-isopentyl-L-homothiocitrulline.

S-Methyl-L-thiocitrulline may be prepared as set forth in Example I. S-Methyl-L-homothiocitrulline may be prepared as set forth in Example II. Other S-alkyl-L-thiocitrullines may be prepared as set forth in Example I by substituting the corresponding iodoalkane for the iodomethane used in Example I (i.e., iodoethane to produce S-ethyl-L-thiocitrulline, iodopropane to produce S-propyl-L-thiocitrulline, etc.) Other S-alkyl-L-homothiocitrullines may be prepared as set forth in Example II by substituting the corresponding iodoalkane for the iodomethane used in Example II.

Examples of specific compounds where one of R, R' and R" provides an alkyl substituent on ornithine or lysine moiety are α-methyl-S-methyl-L-thiocitrulline (the above structural formula where R is $CH_3$, R' is $CH_2$ and R" is $CH_2$ and x is zero and Q is $CH_3$), α-propyl-S-propyl-L-thiocitrulline, β-methyl-S-methyl-L-thiocitrulline (the above structural formula where R is H, R' is C(H)($CH_3$) and R" is $CH_2$ and x is zero and Q is $CH_3$), β-ethyl-S-isobutyl-L-thiocitrulline, γ-methyl-S-methyl-L-thiocitrulline (the above structural formula where R is H, R' is $CH_2$ and R" is C(H)($CH_3$) and x is zero and Q is $CH_3$), γ-butyl-S-methyl-L-thiocitrulline, α-methyl-S-methyl-L-homothiocitrulline (the above structural formula where R is $CH_3$, R' is $CH_2$ and R" is $CH_2$ and x is 1 and Q is $CH_3$), α-pentyl-S-methyl-L-homothiocitrulline, β-methyl-S-methyl-L-homothiocitrulline (the above structural formula where R is H, R' is C(H)($CH_3$) and R" is $CH_2$ and x is 1 and Q is $CH_3$), β-methyl-S-pentyl-L-homothiocitrulline, γ-methyl-S-methyl-L-homothiocitrulline and γ-ethyl-S-ethyl-L-homothiocitrulline (the above structural formula where R is H, R' is $CH_2$ and R" is C(H)($CH_2CH_3$) and x is 1 and Q is $C_2H_5$) and the corresponding D,L-compounds.

The $N^δ$-benzyloxycarbonyl-L-ornithine of Example I may be prepared by reacting benzyloxycarbonyl chloride with copper salt of L-ornithine. The $N^ε$-benzyloxycarbonyl-L-lysine of Example II may be prepared by reacting benzyloxycarbonyl chloride with copper salt of L-lysine. These are well known reactions.

The D,L-compounds where one of R, R' and R" provides an alkyl substituent on ornithine or lysine moiety are prepared by utilizing the appropriate one of α-alkyl-DL-ornithine, β-alkyl-DL-ornithine, γ-alkyl-DL-ornithine, α-alkyl-DL-lysine, β-alkyl-DL-lysine or γ-alkyl-DL-lysine in place of L-ornithine or L-lysine in the synthesis of the compounds where none of R, R' and R" provides an alkyl substituent on ornithine or lysine moiety. The synthesis of the α-alkylornithines, the β-alkylornithines, the γ-alkylornithines, the α-alkyllysines, the β-alkyllysines and the γ-alkyllysines are described in Griffith U.S. patent application Ser. No. 07/889,345. α-Methyl-DL-ornithine is commercially available from Sigma Chemicals, St. Louis, Mo. The synthesis of RS-β-methyl-DL-ornithine and RS-γ-methyl-DL-ornithine are described in detail in said Ser. No. 07/889,345. L-compounds can be made by using L-reactants which can be obtained by resolution of the corresponding D,L-compounds. Admixtures of 50 to 100% L-enantiomer with the remainder being D-enantiomer can be prepared by admixing L-compound with D,L-compound. Admixtures containing less than 50% L-enantiomer can be made by synthesizing D-enantiomer (by starting with D-compound reactant) and admixing this with L-compound or D,L-compound.

The compounds herein are not biologically active as arginine analogs with respect to protein synthesis. Therefore, there is no possibility of these interfering with incorporation of arginine into proteins.

We turn now to the methods herein.

As previously indicated, embodiments herein are directed to methods of treatment of a subject for systemic hypotension caused by pathological overproduction of nitric oxide from arginine by the enzyme nitric oxide synthase induced in vascular cells and, perhaps, other tissues, in said subject with a cytokine or by a bacterial endotoxin. The inducement by cytokines, e.g., gamma-interferon, tumor necrosis factor, interleukin-1 or interleukin-2 can occur because of therapy with said cytokines, e.g., chemotherapeutic treatment with tumor necrosis factor or interleukin-2. In such therapy, the cytokine is administered in conventional amounts for said therapy. However, whereas the period for administration of said therapy is normally limited by the eventual occurrence of severe hypotension and vascular leak, the method herein allows concomitant administration of compound of the invention herein (the term prophylaxis includes said concurrent administration) to delay or eliminate the occurrence of these symptoms. The inducement by endotoxin from bacterial infection or other bacterial toxin is known as septic shock and is the leading cause of death in intensive care units, some 250,000 deaths in one year recently in the U.S. This can be an expected condition in cases where the immune system is compromised, e.g., because of immunosuppression therapy or in AIDS. Septic shock also occurs in immunocompetent people.

We turn now to the method herein for prophylaxis or treatment of a subject for systemic hypotension caused by biological overproduction of nitric oxide from arginine by nitric oxide synthase induced in vascular cells in said subject with a cytokine or by a bacterial endotoxin wherein the method comprises administering to said subject a therapeutically effective amount of a compound of the invention herein. For treatment of systemic hypotension which is already occurring, the compound is administered in a blood pressure raising amount, generally 1 mg/kg to 100 mg/kg for L-enantiomer (preferably 2 mg/kg to 20 mg/kg for S-methyl-L-thiocitrulline and 2 mg/kg to 20 mg/kg for S-methyl-L-homothiocitrulline) by a route of administration obtaining a fast response, normally parenteral, preferably intravenous. For treatment in cases where systemic hypotension is expected (i.e., for prophylaxis, i.e., prevention or delay of the condition occurring or to provide ameliorated occurrence of the condition), administration is to provide a plasma level of compound of invention herein sufficient to eliminate or delay the occurring of the hypotension or to reduce the severity of the hypotension which occurs, generally a plasma concentration ranging from 1 $\mu$M to 100 $\mu$M for L-enantiomer (preferably 10 $\mu$M to 50 $\mu$M for S-methyl-L-thiocitrulline and 10 $\mu$M to 50 $\mu$M for S-methyl-L-homothiocitrulline) by a route of administration which can be parenteral (e.g., intravenous) but also can be oral (doses to provide this concentration may be determined by considering the half-life of the compounds in the body).

We turn now to the method herein for treatment of a subject for systemic hypotension caused by pathological overproduction of nitric oxide from arginine by nitric oxide synthase induced in vascular cells in said subject with a cytokine or by a bacterial endotoxin wherein the method comprises administering to a subject in need of said treatment of a conventional amount of at least one $\alpha_1$-adrenergic agonist and an amount of compound of the invention herein effective to restore vascular contractile sensitivity to the effects of said $\alpha_1$-adrenergic agonists. The $\alpha_1$-adrenergic agonists are used for the same purpose now (i.e., to increase blood pressure in a hypotensive patient) but eventually stop working because of loss of vascular contractile sensitivity. The $\alpha_1$-adrenergic agonists are used in the same dosages as they are used now for the same purpose, i.e., in conventional therapeutically effective amounts. Suitable $\alpha_1$-adrenergic agonists are epinephrine, norepinephrine, dopamine, phenylephrine, metaraminol, methoxamine, ephedrine, and mephentermine. Use with the pressor angiotensin II is also envisioned. Doses for dopamine typically range from 2 $\mu$g/kg/min to 50 $\mu$g/kg/min. Doses for epinephrine typically range from 0.25 mg to 1.0 mg. Doses for norepinephrine typically range from 2 $\mu$g/min to 4 $\mu$g/min and are typically used if dopamine dose exceeds 20 $\mu$g/kg/min. Doses for phenylephrine can range from 0.1 to 10 $\mu$g/kg. Doses for angiotensin II can range from 0.01 to 1 $\mu$g/kg. The route of administration of the most popular $\alpha_1$-adrenergic agonists (epinephrine, norepinephrine and dopamine) is intravenous and for the others the route of administration is intravenous or in some cases subcutaneous. The compound of the invention herein is administered in an amount effective to restore vascular contractile sensitivity to the effects of the $\alpha_1$-adrenergic agonist (i.e., to increase and/or prolong the efficacy of the $\alpha_1$-adrenergic agonists), generally 1 mg/kg to 100 mg/kg for L-enantiomer (preferably 2 mg/kg to 20 mg/kg for S-methyl-L-thiocitrulline and 2 mg/kg to 20 mg/kg for S-methyl-L-homothiocitrulline) by a route of administration obtaining a fast response, normally parenteral, preferably intravenous.

We turn now to the method herein for suppressing an immune response, e.g., where the immune response is part of an inflammatory response, in a subject in need of said suppressing, said method comprising administering to a subject in need of said suppressing an immunosuppressive effective amount of compound of the invention herein. This method may be directed to prophylaxis or treatment of a subject for inflammation, e.g., arising from autoimmune conditions including rheumatoid arthritis and from host-defense immune mechanisms, e.g., allograft rejection reactions, caused by immunologically induced nitric oxide production in immune cells, said method involving inhibiting said nitric oxide production in said cells by administering to a subject possibly developing or having such inflammation, a nitric oxide synthesis inhibiting therapeutically effective (inflammation attenuation) amount of compound of the invention herein. The dosages of L-enantiomer compound herein for use in this method generally range from 1 mg/kg to 1000 mg/kg (preferably 2 mg/kg to 200 mg/kg for S-methyl-L-thiocitrulline and 2 mg/kg to 200 mg/kg for S-methyl-L-homothiocitrulline). Methods of administration include oral, intramuscular, subcutaneous and intravenous. The dosages set forth above are daily dosages and are administered for a period of time to cause suppression of immune response and attenuation of inflammation, i.e., two days or more, e.g., for two days to three weeks.

We turn now to the method herein for prophylaxis or treatment of a subject for a stroke wherein the method comprises administering to said subject of a therapeutically effective amount of compound of the invention herein. For a stroke in progress, administration is preferably within 6 hours of the onset of the stroke, very preferably within 4 hours of the onset of the stroke. Since time is of the essence, administration typically is as soon as practical after diagnosis. The therapeutically effective amount is a neuronal cell protecting amount, i.e., an amount which causes increase in neuronal cell survival compared to where the stroke is untreated. Generally, the dose for L-enantiomer ranges from 1 mg/kg to 100 mg/kg (preferably 2 mg/kg to 20 mg/kg for S-methyl-L-thiocitrulline and 2 mg/kg to 20 mg/kg for S-methyl-L-homothiocitrulline). Administration is by a route offering a fast response, e.g., parenteral, preferably intravenous or intraarterial. Prophylaxis involves treatment of those of high risk for a stroke because of medical history and administration is that amount sufficient to provide an uninterrupted plasma level of compound herein in a neuronal cell protecting concentration, generally 1 $\mu$M to 100 $\mu$M for L-enantiomer (preferably 10 $\mu$M to 50 $\mu$M for S-methyl-L-thiocitrulline and 10 $\mu$M to 50 $\mu$M for S-methyl-L-homothiocitrulline) and administration is preferably carried out orally on a daily basis.

Dosages are given above for the L-enantiomer. For admixtures of L-enantiomer and D-enantiomer, dosages are calculated by dividing those given above by the weight percent of L-enantiomer in the admixture.

The invention is illustrated in the following examples.

Example I

Synthesis of S-Methyl-L-thiocitrulline $N^\delta$-(Benzyloxycarbonyl)-L-ornithine tert-butyl ester was prepared according to a general published procedure (Bodanszky, M.; Bodanszky, A.; The Practice of Peptide Synthesis; Spring Verlag: New York, 1984). Specifically, $N^\delta$-(benzyloxycarbonyl)-L-ornithine (10.0 gm, 37.6 mmol, Sigma Chemicals, Inc.) was mixed with tert-butyl acetate (564 ml) and perchloric acid (5.91 ml, 69–72% aqueous solution) at room temperature. The reaction mixture became homogenous after 15 minutes and was stirred at room temperature for 2 days. Water (300 ml) was added to the reaction mixture, and the two layers obtained were separated. The organic layer was extracted twice (2×200 ml) with water, and the combined aqueous layers were adjusted to pH 9.5–10.0 with 50% NaOH. The aqueous layer was then filtered to remove a small amount of insoluble material, and the filtrate was extracted with ethyl acetate (3×300 ml). The combined ethyl acetate extracts were dried over MgSO$_4$ and were concentrated by rotary evaporation at reduced pressure to yield 7.5 g of $N^\delta$-(benzyloxycarbonyl)-L-ornithine tert-butyl ester as an oil (65% yield). $^1$H NMR (DCCl$_3$) $\delta$1.44 (s,9H), 1.5–1.9 (m,4H), 3.23 (t,2H), 3.31 (t,1H), 5.09 (s,2H and s,1H broad), 7.35 (s,5H).

$N^\alpha$-(tert-Butyloxycarbonyl)-$N^\delta$(benzyloxycarbonyl)-L-ornithine tert-butyl ester:

$N^\delta$-(Benzyloxycarbonyl-L-ornithine tert-butyl ester (7.50 g, 23.3 mmol) was dissolved in 27 ml of methylene chloride, and the solution was cooled to 0° C. To that solution was added dropwise tert-butyl pyrocarbonate (5.87 g, 26.9 mmol) in 10 ml of methylene chloride. The reaction mixture was stirred at 0° C. for 1 hour, and stirring was continued for 3 additional hours at room temperature. The solvent was evaporated at reduced pressure and the oily residue was chromatographed on a column of silica gel (25 cm×30 mm) using hexane:ethyl acetate (3:1) as solvent. Fractions of approximately 5 ml were collected, and those containing product were identified by thin layer chromatography (see below). Chromatographic fractions containing product were pooled and evaporated to a thick oil by rotary evaporation at reduced pressure. The yield was 8.63 gm (93.5%). $^1$H NMR (DCCl$_3$) $\delta$1.44 (s,9H), 1.46 (s,9H), 1.5–1.9 (m,4H), 3.23 (t,2H), 4.17 (t,1H), 4.88 (s,1H broad), 5.09 (s,2H and s,1H broad) 7.35 (s,5H).

Thin layer chromatography was carried out on silica gel plates using hexane:ethyl acetate (3:1) as solvent. $N^\delta$-(benzyloxycarbonyl)-$N^\alpha$-(tert-butyloxycarbonyl)-L-ornithine tert-butyl ester chromatographed with an R$_f$=0.33 and was detected by fluorescence using a hand-held UV light.

$N^\delta$-(tert-butyloxycarbonyl-L-ornithine tert-butyl ester:

The ester from the previous step (8.63 gm, 20.45 mmol) was dissolved in 50 ml of methanol and 10% Pd/C catalyst (0.90 gm) was added. The mixture was hydrogenated on a Parr hydrogenator at 20 psi H$_2$ for 4 hr. Following reduction, the reaction mixture was filtered over Celite and evaporated to dryness by rotary evaporation at low pressure to provide $N^\alpha$-(tert-butyloxycarbonyl)-L-ornithine tert-butyl ester as an oil. The yield was 5.88 gm (100%). $^1$H NMR (DCCl$_3$) $\delta$1.44 (s,9H), 1.46 (s,9H), 1.5–1.9 (m,4H), 2.73 (t,2H), 4.17 (t,1H), 5.20 (s,1H broad).

$N^\alpha$-(tert-butyloxycarbonyl)-$N^\delta$(thioureido)-L-norvaline tert-butyl ester:

This product was prepared as described by Feldman (Feldman, P. L.; Tetrahedron Lett. 1991, 32, 875–878). $N^\alpha$-(tert-butyloxycarbonyl)-L-ornithine tert-butyl ester (5.80 gm) was dissolved in 100 ml chloroform and added to a solution of 5.70 gm of calcium carbonate and 2.2 ml of thiophosgene (28.7 mmol) dissolved in 100 ml of water. The mixture was stirred vigorously overnight. The next day the reaction mixture was filtered and the layers were allowed to separate. The aqueous layer was extracted with chloroform (2×50 ml) and the combined organic layers were dried (MgSO$_4$) and concentrated to an oil by evaporation at reduced pressure. The residue was taken up in dry methanol (200 ml) and cooled to 0° C. Ammonia gas was then passed through the solution for 20 minutes, and the solution was stirred for 3 hours at 0° C. Following reaction with ammonia, the solvent was evaporated under reduced pressure and the residue was dissolved in ethyl acetate:hexane (4:1). That solution was chromatographed on a column of silica gel (25 cm×30 mm) using the same ethyl acetate/hexane mixture as eluent. Fractions of approximately 5 ml were collected, and those containing product were identified by thin layer chromatography (see above, R$_f$=0.30). Product-containing fractions were pooled and evaporated to dryness under reduced pressure to yield $N^\alpha$-(tert-butyloxycarbonyl)-$N^\delta$-(thioureido)-L-norvaline tert-butyl ester in 70% yield. $^{13}$C NMR (DCCl$_3$) 183.4–180.4 (one carbon), 17.1–6,155-9, 82.2–80.0, 53.6–52.5 (one carbon), 44.6–43.1 (one carbon), 30.4, 28.1, 27.8, 24.6.

$N^\alpha$-(tert-butyloxycarbonyl)-$N^\alpha$-(N-tert-butyloxycarbonyl-S-methyl) isothioureido-L-norvaline-tert-butyl ester:

A solution of N$\alpha$-(tert-butyloxycarbonyl)-$N^\delta$-(thioureido)-L-norvaline-tert-butylester (2.35 g, 6.62 mmol) and iodomethane (1 ml, 16.8 mmol) in CH$_3$CN (15 ml) was stirred at 23° C. for 16 hours. The solution was concentrated and the residue dissolved in dioxane (16 ml). To that solution was added saturated NaHCO$_3$ in water (16 ml) and di-tert-butyl pyrocarbonate (2.08 g., 9.54 mmol). The reaction mixture was vigorously stirred at room temperature for 12 hours. The dioxane was removed via evaporation under reduced pressure, and the aqueous solution was extracted with ethyl acetate (3×75 ml). The combined organic layers were dried over MgSO$_4$ and evaporated under reduced pressure. The residue was chromatographed on silica gel using hexane/ethyl acetate (3:1) (Rf=0.50) to provide the product as an oil (3.08 g., 70%): $^{13}$C NMR (DCCl$_3$), $\delta$173.0, 171.1, 161.8, 155.0, 81.7, 79.3, 78.7, 53.0, 42.9, 29.7, 28.0, 27.9, 24.8, 13.2.

$N^\delta$-(S-methyl)-isothioureido-L-norvaline:

The compound prepared in the previous step (0.470 g, 10.2 mmol) was dissolved in 4N HCl/dioxane (3 ml)

and stirred at room temperature for 20 hours. The reaction mixture was diluted with ethyl ether (10 ml), and the solvents were evaporated under reduced pressure. The addition and removal of ethyl ether was repeated two more times. Methanol (10 ml) was then added and evaporated under reduced pressure to provide $N^\delta$-(S-methyl)-isothioureido-L-norvaline, also called S-methyl-L-thiocitrulline, as a hydrochloride salt. (282 mg, 89.5%). $^1$HNMR (D$_2$O) $\delta$1.5–1.9(m,4H), 2.36(s,3H), 3.23(t,2H), 3.88(t,1H); mass spectrum, 206(MH+).

Reference Example I

S-Methyl-D-thiocitrulline was prepared as described for S-methyl-L-thiocitrulline (Example I) except that the starting material was $N^\delta$-(benzyloxycarbonyl)-D-ornithine (Sigma Chemicals, Inc.).

EXAMPLE II

Synthesis of S-Methyl-N$^\epsilon$-(thioureido)-L-norleucine
(S-Methyl-L-homothiocitrulline)

Nα-(Benzyloxycarbonyl)-L-lysine tert-butyl ester:

$N^\alpha$-(Benzyl-oxyarbonyl)-L-lysine (5.0 gm, 17.84 mmol) was dissolved in 268 ml of tert-butyl acetate containing 2.80 ml of perchloric acid (69–72% aqueous solution). The solution was stirred for 2 days at room temperature and then was extracted with water (3×200 ml). The combined aqueous layers were adjusted to pH 10 with 50% sodium hydroxide. The aqueous solution was then extracted with ethyl acetate (3×200 ml) and the organic layers dried over MgSO$_4$. After filtration to remove MgSO$_4$, the solvent was removed by evaporation at reduced pressure to provide $N^\alpha$-(benzyloxycarbonyl)-L-lysine tert-butyl ester as a clear oil (2.16 gm, 36%). $^1$H NMR (CDCl$_3$) 1.35 (s,9H), 1.40–2.0 (m,6H), 2.60 (t,2H), 4.10 (m,1H), 4.98 (s,2H), 5.29 (bs,1H), 7.35 (s,5H).

N$^\epsilon$-(Thioureido)-N$^\alpha$-(benzyloxycarbonyl)-L-norleucine tert-butyl ester:

$N^\alpha$-(Benzyoxycarbonyl)-L-lysine tert-butyl ester (2.16 gm, 6.43 mmol) was dissolved in 30 ml of chloroform and added to a prepared solution of calcium carbonate (1.80 g, 18.0 mmol) in 30 ml of water containing 0.70 ml of thiophosgene; the mixture was stirred for 6 hours at room temperature. The reaction mixture was then filtered and the layers separated. The aqueous layer was extracted with chloroform (2×30 ml) and the combined organic layers were dried over MgSO$_4$. After filtration to remove MgSO$_4$, the dry solution was evaporated under reduced pressure to yield a clear oil. The residue was dissolved in 55 ml of methanol and cooled to 0° C. Ammonia gas was passed into the solution for 15 minutes and the reaction mixture was stirred for 3 hours at 0° C. The methanol was then evaporated at reduced pressure and the residue was chromatographed on a column of silica gel (25 cm ×30 mm) using ethyl acetate:hexane (4:1) (R$_f$=0.33) as the eluent. Fractions containing product were identified by thin layer chromatography and were pooled. Evaporation of the product-containing fractions yielded $N^\alpha$-(benzyloxycarbonyl)-N$^\epsilon$-thioureido-L-norleucine tert-butyl ester as a foamy solid. $^{13}$C NMR (CDCl$_3$) $\delta$182.70–179.6 (one carbon), 171.35, 155.99, 135.77, 129.19, 128,85, 127.08, 126.61, 81.92, 68.5–64.65 (one carbon) 54.73–52.97 (one carbon), 46.30–41.50 (one carbon), 30.10, 28.40, 26.73, 25.0.

N$^\delta$-S-Methyl)-thioureido-L-norleucine (S-Methyl-L-homothiocitrulline):

$N^\alpha$-(Benzyloxycarbonyl)-N$^\epsilon$-thioureido-L-norleucine tert-butyl ester (340 mg, 0.86 mmol) was stirred with iodomethane (0.1 ml) in acetonitrile (2 ml) for 16 hours at room temperature. The solvent was then evaporated under reduced pressure, and the residue was treated with 4M HCl/dioxane (5 ml) at 75° C. After 1 hour the solvent was evaporated and the resulting residue was triturated with ethyl ether (10 ml). The ether was evaporated and methanol (10 ml) was added and evaporated to yield a hygroscopic solid (226 mg, 90%); $^1$H NMR (D$_2$O) $\delta$1.34–1.80(m,6H), 2.42(S,3H), 3.20(m,2H), 3.86(t, 1H); mass spectrum, m/e 220 (M+H+).

EXAMPLE III

Inhibition of Smooth Muscle Nitric Oxide Synthase by S-Methyl-L-thiocitrulline and Other Compounds The activity of S-methyl-L-thiocitrulline, L-thiocitrulline, and $N^G$-methyl-L-arginine as inhibitors of smooth muscle nitric oxide synthase was determined in vitro by monitoring the conversion of [$^{14}$C]arginine to [$^{14}$C]citrulline.

Smooth muscle nitric oxide synthase, an example of induced nitric oxide synthase (iNOS) was obtained as follows: aortic smooth muscle cells were cultured by explanting segments of the medial layer of the aortae of adult male Fischer 344 rats. Aortae were removed aseptically and freed of adventitial and endothelial cells by scraping both the luminal and abluminal surfaces. Medial fragments (1–2 mm) were allowed to attach to dry Primaria 25 cm$^2$ tissue culture flasks (Falcon; Oxnard, Calif.) which were kept moist with growth medium until cells emerged. Cultures were fed twice weekly with medium 199 containing 10% fetal bovine serum, 25 mM HEPES, 2 mM L-glutamine, 40 μg/ml endothelial cell growth supplement (Biomedical Technologies; Stoughton, Mass.) and 10 μg/ml gentamyocin (GIBCO; Grand Island, N.Y.). When primary cultures became confluent, they were passaged by trypsinization. Cells in passage 10–15 were seeded at 20,000/well. When the cells became confluent (density of 60–80×10$^3$ cells in a well), the medium was removed by suction and fresh medium consisting of 200 μl of RPMI 1640 (Whittaker Laboratories) containing 10% bovine calf serum, 25 mM HEPES buffer (pH 7.4), 2 mM glutamine, 80 U/ml penicillin, 80 μM/ml streptomycin, 2 μg/ml fungizone, 40 ng/ml interleukin-1 and 50 ng/ml interferon-gamma was introduced. Interleukin-1 and interferon-gamma are effective inducers of iNOS.

In a final volume of 200 μl, the reaction mixtures contained the following: 20 mM sodium HEPES, pH 7.15, 0.1 mM EGTA (ethylene glycol bis($\beta$-aminoethyl ether)-N,N,N',N'-tetraacetic acid), 0.1 mM dithiothreitol, 100 μM tetrahydrobiopterin, 500 μM NADPH, 25 μM FAD, 25 μM FMN and 0.03–00.05 units of nitric oxide synthase (1 unit equals the amount of enzyme necessary to convert 1 nmol of arginine to citrulline and nitric oxide per min). The reaction was begun by adding to the reaction mixture 20 μM L-[$^{14}$C]arginine and, except in the case of the control, 0.1 μM (S-methyl-L-thiocitrulline, 1.0 μM S-methyl-L-thiocitrulline or 10 μM S-methyl-L-thiocitrulline. The reaction mixtures were maintained at 25° C. and at 3.5, 7.0, and 10.5 minutes 50 μl portions were removed from each reaction mixture and added to 200 μl of 100 mM sodium HEPES, pH 5.5 containing 5 mM EGTA. The decrease in pH stops the reaction. The reaction mixtures were then placed in a boiling water bath for 1 minute which caused the protein to precipitate; the precipitate was removed by centrifugation. A 225 μl portion of the supernatant was then removed and applied to a small column of Dowex 50 (Na+ form, 200–400 mesh, 0.5×3.5 mm). L-[$^{14}$C]citrulline, a product of the reaction, was eluted from the columns using 2.0 ml of water. The eluant was collected directly into a scintillation vial, 10 ml of scintillation fluid (Econo-Safe, Research Products International Corp.) were added and the contained radioactivity was determined by liquid scintillation counting. Knowing the specific activity of the L-arginine in the original reaction mixture, it was possible to convert the cpm citrulline data to pmol product.

Figure 1:
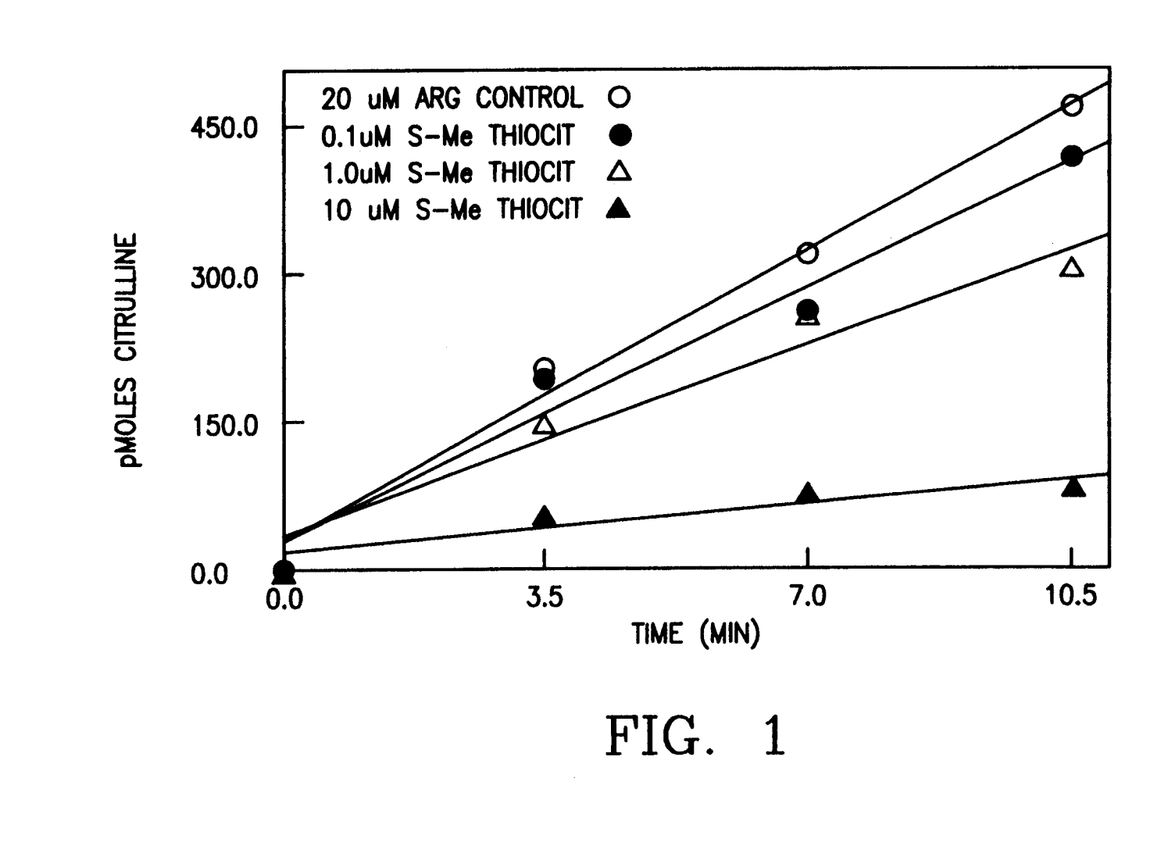
FIG. 1 is a graph of product formation versus time, depicting results of Example III.

Results are shown in FIG. 1 wherein product formation was plotted as a function of time. In FIG. 1 the line denoted by open circles is the arginine control, the line denoted by filled in circles is for the experiment with 0.1 μM S-methyl-L-thiocitrulline, the line denoted by open triangles is for the experiment with 1.0 μM S-methyl-L-thiocitrulline, and the line denoted by filled in triangles is for the experiment with 10 μM S-methyl-L-thiocitrulline.

As shown in FIG. 1, in the absence of test compound (20 μM arginine control line) product formation was constant over a 10.5 minute period observed. Addition of 0.1, 1.0 and 10 μM S-methyl-L-thiocitrulline caused about 10%, 32% and 84% inhibition, respectively.

Under similar reaction conditions, 10 and 30 μM L-thiocitrulline caused 34 and 70% inhibition respectively, showing that L-thiocitrulline is less potent than S-methyl-L-thiocitrulline.

Addition of 100 μM N$^G$-methyl-L-arginine (L-NMA, the prototypic nitric oxide synthase inhibitor) caused inhibition approximately equal to that of 10 μM S-methyl-L-thiocitrulline.

EXAMPLE IV

Figure 2:
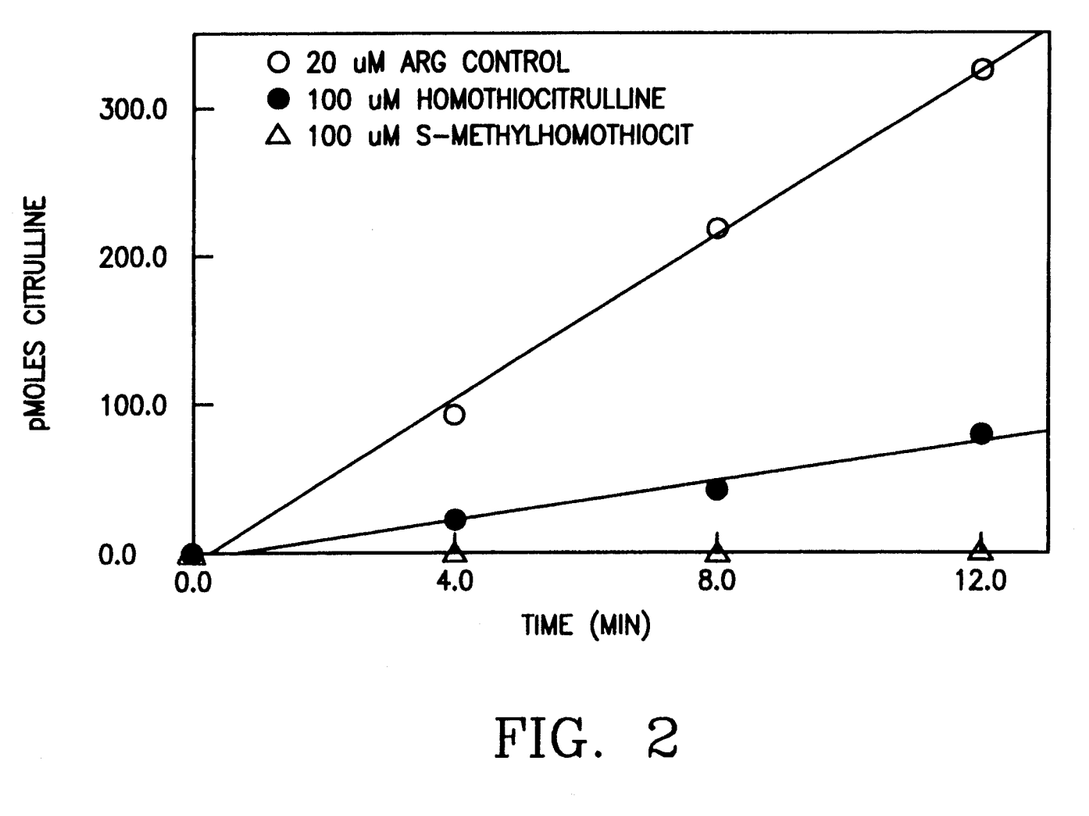
FIG. 2 is a graph of product formation versus time, depicting results of Example IV.

Inhibition of Smooth Muscle Nitric Oxide Synthase by S-Methyl-L-homothiocitrulline and L-Homothiocitrulline Using the same protocol as described for the studies described in Example I, 100 μM homothiocitrulline and 100 μM S-methyl-L-homothiocitrulline were compared as inhibitors of smooth muscle nitric oxide synthase. Time points were taken at 4, 8 and 12 minutes rather than at 3.5, 7 and 10.5 minutes. The results of the study with L-homothiocitrulline and S-methyl-L-homothiocitrulline are shown in FIG. 2. In FIG. 2, the line denoted by the open circles is the control indicating the rate of citrulline formation in the absence of inhibitors. The line denoted by the filled circles is for the experiment with 100 μM L-homothiocitrulline, and the line denoted by the open triangles is for the experiment with 100 μM S-methyl-L-homothiocitrulline. The experiment shows that whereas L-homothiocitrulline causes significant inhibition under these circumstances, an identical concentration of S-methyl-L-homothiocitrulline causes complete inhibition; the S-methyl-L-homothiocitrulline is therefore a more potent inhibitor than L-homothiocitrulline.

EXAMPLE V

The Effect of S-Methyl-L-thiocitrulline on Blood Pressure

Figure 3:
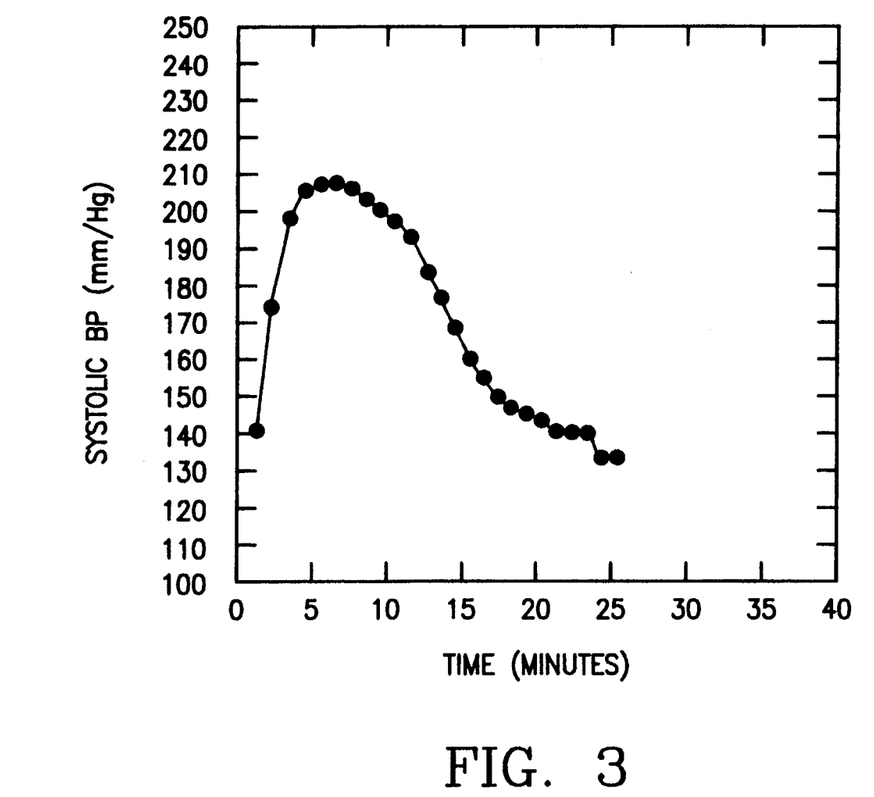
FIG. 3 is a graph of systolic blood pressure (denoted BP) versus time, depicing results of Example V.

To test the ability of S-methyl-L-thiocitrulline to block basal nitric oxide formation in vivo, its effects were tested in anesthetized Sprague-Dawley rats. Rats (250–300 gm) were anesthetized with Inactin (100 mg/kg i.p.) and placed on a heated surgical table to maintain body temperature of 36.5° C. Femoral arterial and venous catheters were implanted (tips were distal to the renal artery) for measurement of blood pressure and infusion of compounds, respectively. Blood pressure was measured using a pressure transducer (Cobe, Inc.) connected to a microcomputer using data acquisition software (AT-CODAS; Data Q Instruments, Akron, Ohio). After waiting several minutes to establish a stable baseline blood pressure, S-methyl-L-thiocitrulline (20 mg/kg) was given by bolus injection through the venous catheter. The solution administered was 100 mM. Changes in systolic, diastolic, and mean arterial pressure were monitored for approximately 25 minutes. The effects on systolic blood pressure are shown in FIG. 3. As shown, S-methyl-L-thiocitrulline caused a significant (70 mm Hg, 50%) increase in blood pressure which lasted 10–15 minutes. Under similar circumstances, N$^G$-methyl-L-arginine, the prototype inhibitor caused a somewhat smaller increase in blood pressure, which lasted about the same time. There was no significant effect on heart rate. The studies indicate that S-methyl-L-thiocitrulline is an effective pressor agent in vivo. Based on earlier studies with N$^G$-methyl-L-arginine, the prototypic nitric oxide synthase inhibitor, S-methyl-L-thiocitrulline is viewed as blocking the basal release of nitric oxide from vascular endothelial cells. Decreased release of basal nitric oxide removes an important vasodilatory mediator involved in normal blood pressure regulation and results in increased vascular tone. Increased vascular tone (vasoconstriction) increases systemic vascular resistance; blood pressure consequently increases.

EXAMPLE VI

The Effect of S-Methyl-L-thiocitrulline on Blood Pressure in Cytokine Therapy

A human is continuously administered interleukin-2 (1×10$^6$ units) for 5 days. S-Methyl-L-thiocitrulline (2 to 20 mg/kg/day) is administered by continuous infusion at a rate sufficient to maintain a systolic blood pressure of 80–120 mm Hg. The severe hypotension characteristic of the end of interleukin-2 therapy is significantly reduced.

EXAMPLE VII

The Effect of S-Methyl-L-thiocitrulline on Increasing Response to Pressor Agents Sprague-Dawley rats are injected intraperitoneally with bacterial lipopolysaccharide (a bacterial endotoxin) (15 mg/kg) alone, together with phenylephrine (6 μg/kg), and together with S-methyl-L-thiocitrulline (20 mg/kg) and phenylephrine (6 μg/kg). The treatment with the combination of S-methyl-L-thiocitrulline and phenylephrine significantly reduces the fall in blood pressure from bacterial lipopolysaccharide administration to a greater degree than phenylephrine alone.

EXAMPLE VIII

Inhibition of Brain Nitric Oxide Synthase by S-Methyl-L-thiocitrulline and Other Compounds The activity of S-methyl-L-thiocitrulline, L-thiocitrulline, and N$^G$-methyl-L-arginine as inhibitors of rat brain nitric oxide synthase was determined in vitro by monitoring the conversion of [$^{14}$C]arginine to [$^{14}$C]citrulline.

Purified rat brain nitric oxide synthase, isolated as described (McMillan, K., Bredt, D. S., Hirsch, D. J., Synder, S. H., Clark, J. E., and Masters, B. S., *Proc. Natl. Acad. Sci. USA* Vol 89, pp., 11141–11145, December 1992) was obtained from Dr. Bettie Sue Masters, The University of Texas health Science Center at San Antonio, Department of Biochemistry, 7703 Floyd Curl Drive, San Antonio, Tex. 78284.

Figure 4:
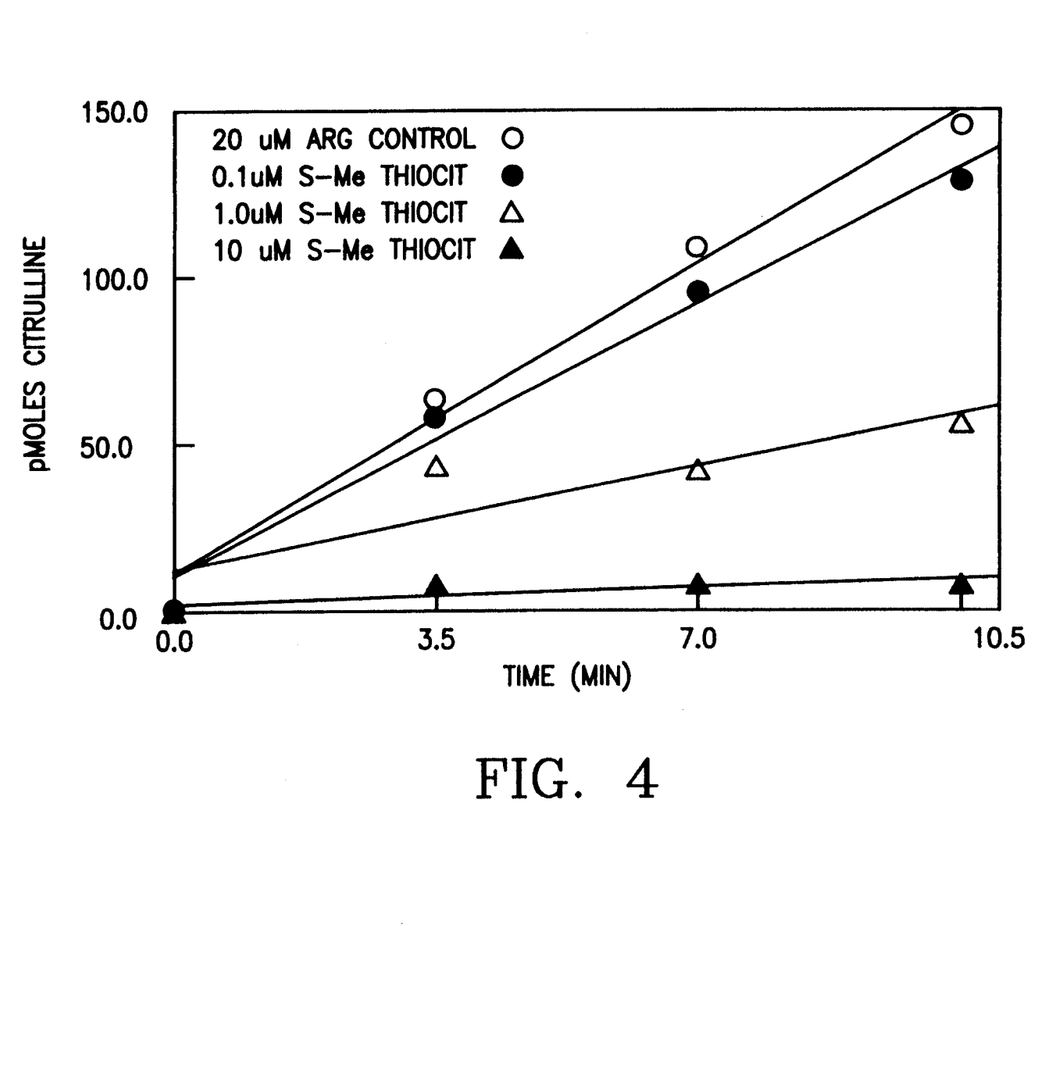
FIG. 4 is a graph of product formation versus time, depicting results of Example VIII.

In a final volume of 200 μl, the reaction mixtures contained the following: 20 mM sodium HEPES, ph 7.5, 0.1 mM EGTA, 0.1 mM dithiothreitol, 10 μg/ml calmodulin, 2 mM calcium chloride, 100 μM tetrahydrobiopterin, 100 μg/ml bovine serum albumin, 500 μM NADPH, 25 μM FAD, 25 μM FMN and 0.03–0.05 units of nitric oxide synthase (1 unit equals the amount of enzyme necessary to convert 1 nmol of arginine to citrulline and nitric oxide per min). The reaction was begun by adding to the reaction mixture 20 μM L-[$^{14}$C]arginine and, except in the case of the control, 0.1 μM S-methyl-L-thiocitrulline, 1.0 μM S-methyl-L-thiocitrulline or 10 μM S-methyl-L-thiocitrulline. The reaction mixtures were maintained at 25° C. and at 3.5, 7.0, and 10.5 minutes 50 μl portions were removed and added to 200 μl of 100 mM sodium HEPES, pH 5.5, containing 5 mM EGTA. The decrease in pH and the binding of calcium by EGTA stops the reaction. The reaction mixtures were then placed in a boiling water bath for 1 minute which caused the protein to precipitate; the precipitate was removed by centrifugation. A 225 μl portion of the supernatant was then removed and applied to a small column of Dowex 50 (Na+ form, 200–400 mesh, 0.5×3.5 mm). L-[$^{14}$C]Citrulline, a product of the reaction, was eluted from the columns using 2.0 ml of water. The eluant was collected directly into a scintillation vial, 10 ml of scintillation fluid (Econo-Safe, RPI Corp, Mt. Prospect, Ill.) were added and the contained radioactivity was determined by liquid scintillation counting. Knowing the specific activity of the L-[$^{14}$C]arginine in the original reaction mixture, it was possible to convert the cpm citrulline data to pmol product. Results are shown in FIG. 4 wherein product formation is plotted as a function of time. As shown in FIG. 4, the line denoted by open circles is the control, the line denoted by filled in circles is for the experiment with 0.1 μM S-methyl-L-thiocitrulline, the line denoted by open in triangles is for the experiment with 1.0 μM S-methyl-L-thiocitrulline, and the line denoted by filled in triangles is for the experiment with 10 μM S-methyl-L-thiocitrulline.

As shown in FIG. 4, in the absence of inhibitor (20 μM arginine control line), product formation is constant over the 10.5 minute period observed. Addition of 0.1, 1.0 and 10 μM S-methyl-L-thiocitrulline caused about 5%, 65% and 95% inhibition respectively.

Under identical reaction condition, L-thiocitrulline at 10 and 30 μM caused 50 and 75% inhibition, respectively, showing that S-methyl-L-thiocitrulline is a more potent inhibitor than is L-thiocitrulline.

Addition of 100 μM N$^G$-methyl-L-arginine (L-NMA, the prototypic nitric oxide synthase inhibitor) also caused substantial inhibition, but L-NMA was much less effective than 100 μM S-methyl-L-thiocitrulline (not shown).

EXAMPLE IX

Figure 5:
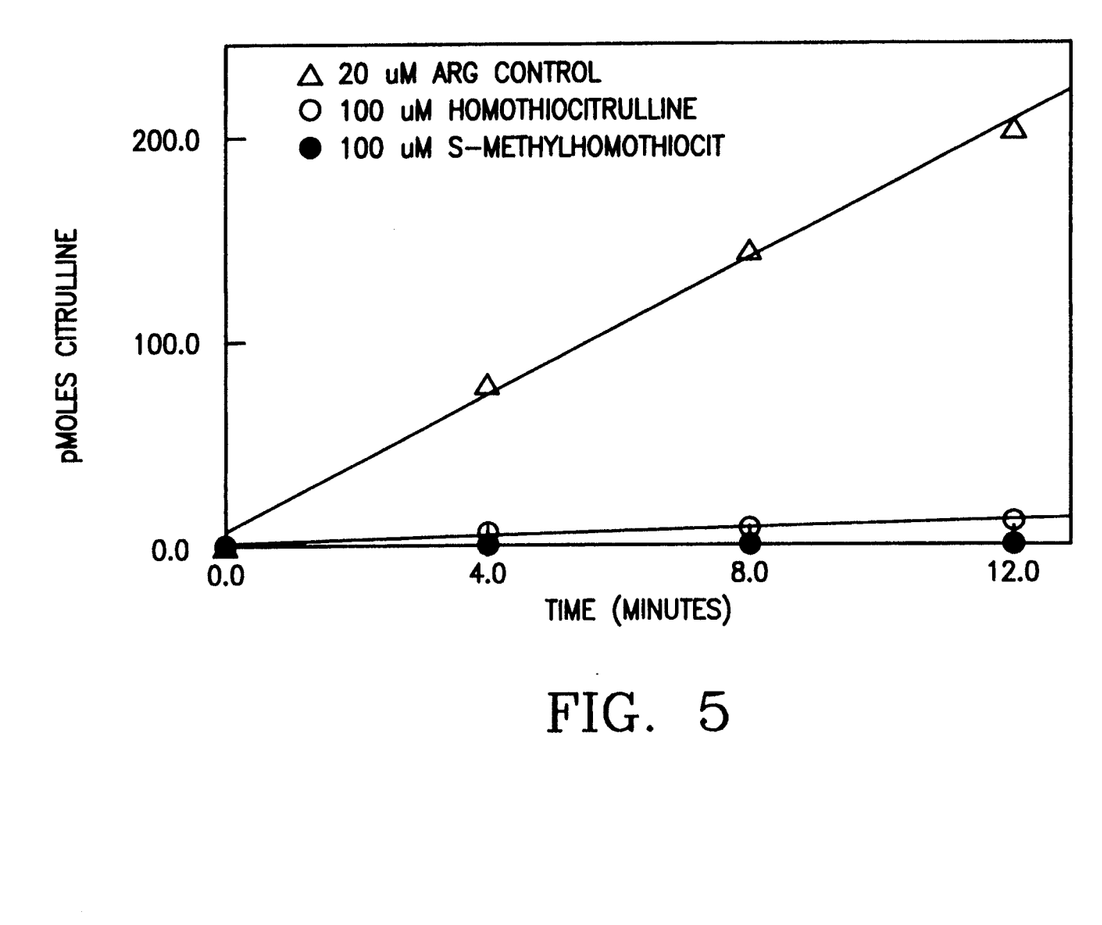
FIG. 5 is a graph of product formation versus time, depicting results of Example IX.

Inhibition of Brain Nitric Oxide Synthase by S-Methyl-L-homothiocitrulline and L-Homothiocitrulline Using the same protocol as for the studies described in Example VIII, L-homothiocitrulline and S-methyl-L-homothiocitrulline were compared as inhibitors of brain nitric oxide synthase. Time points were taken at 4, 8 and 12 minutes rather than at 3.5, 7 and 10.5 minutes. The results of the study with L-homothiocitrulline and S-methyl-L-homothiocitrulline are shown in FIG. 5. In FIG. 5, the line denoted by the open triangles is the control indicating the rate of citrulline formation in the absence of inhibitors. The line denoted by the open circles is for the experiment with 100 μM L-homothiocitrulline, and the line denoted by the filled in circles is for the experiment with 100 μM S-methyl-L-homothiocitrulline. The experiment shows that whereas L-homothiocitrulline causes significant inhibition under these circumstances, an identical concentration of S-methyl-L-homothiocitrulline causes complete inhibition; S-methyl-L-homothiocitrulline is therefore a more potent inhibitor than L-homothiocitrulline.

EXAMPLE X

Treatment of Stroke

Both common carotid arteries are ligated in two groups of female Sprague-Dawley CFY rats. After 10 minutes, ligations are released and flow is again allowed.

In the case of one group, S-methyl-L-thiocitrulline (20 mg/kg) is administered by bolus injection through a venous catheter 30 minutes after occlusion of the arteries. In the case of the other group, no therapeutic agent is administered.

Histological analysis of stroke volume 24 hours following artery occlusion shows significant reduction in stroke volume for the group administered S-methyl-L-thiocitrulline compared to the group receiving no treatment.

EXAMPLE XI

Treatment of Inflammation

Sprague-Dawley rats are injected with 0.25 cc air subdermally in the dorsal area in accordance with an air pouch inflammatory model (Selye, H., Proc. Soc. Exper. Biol. and Med., 82, 328–333 (1953)). Into the air pouch formed, an inflammatory stimulus, croton oil (0.5% in 0.5 ml corn oil), is injected. Simultaneously, the rats in one group are administered intraperitoneally S-methyl-L-thiocitrulline (20 mg/kg) and this administration is repeated every 12 hours for 5 days. The rats in another group are not administered S-methyl-L-thiocitrulline. At the end of the 5 days, the group of rats given S-methyl-L-thiocitrulline have significantly less inflammation than the rats in the other group.

When the same amount of S-methyl-L-homothiocitrulline is substituted for L-thiocitrulline in Examples V, VI, VII, X and XI, similar results are obtained.

Many variations of the above will be obvious to those skilled in the art. Thus, the invention is defined by the claims.

What is claimed is:

1. Physiologically active compounds including N$^\delta$-substituted ornithine or N$^\epsilon$-substituted lysine moieties or monoalkyl carbon-substituted $N^\delta$-substituted ornithine or $N^\epsilon$-substituted lysine moieties, having the formula wherein R is $(CH_2)_y CH_3$ or H, R' is $CH_2$ or $C(H)(CH_2)_y CH_3$, and R" is $CH_2$ or $C(H)(CH_2)_y CH_3$, with y ranging from 0 to 5, and x is 0 or 1 and wherein none or only one of R, R' and R" provides an alkyl substituent on ornithine or lysine moiety, and wherein Q is alkyl having 1 to 5 carbon atoms, and physiologically acceptable acid addition salts thereof.

2. Physiologically active compounds as recited in claim 1 wherein none of R, R' and R" provides an alkyl substituent on ornithine or lysine moiety.

3. Physiologically active compounds as recited in claim 2 wherein x is O.

4. Physiologically active compound as recited in claim 3 which is S-methyl-L-thiocitrulline or physiologically acceptable acid addition salt thereof.

5. Physiologically active compounds as recited in claim 2 wherein x is 1.

6. Physiologically active compound as recited in claim 5 which is S-methyl-L-homothiocitrulline or physiologically acceptable acid addition salt thereof.

7. A method of treatment or prophylaxis of a subject for systemic hypotension or expected systemic hypotension caused by pathological overproduction of nitric oxide from arginine by nitric oxide synthase induced in said subject with a cytokine or by a bacterial endotoxin, said method comprising administering to said subject a therapeutically effective amount of a compound of claim 1.

8. The method of claim 7 wherein the compound is S-methyl-L-thiocitrulline or a physiologically acceptable acid addition salt thereof.

9. The method of claim 7 wherein the compound is S-methyl-L-homothiocitrulline or a physiologically acceptable acid addition salt thereof.

10. A method for suppressing an immune response in a subject in need of said suppressing, said method comprising administering to a subject in need of said suppressing an immunosuppressive effective amount of a compound of claim 1.

11. The method of claim 10 wherein said immune response is part of an inflammatory response caused by induced nitric oxide production from arginine in immune cells.

12. The method of claim 11 wherein the compound is S-methyl-L-thiocitrulline or a physiologically acceptable acid addition salt thereof.

13. The method of claim 11 wherein the compound is S-methyl-L-homothiocitrulline or a physiologically acceptable acid addition salt thereof.

14. A method of prophylaxis or treatment of a subject for a stroke, said method comprising administering to said subject a therapeutically effective amount of a compound of claim 1.

15. The method of claim 14 wherein the therapeutically effective amount is a neuronal cell protecting amount.

16. The method of claim 15 wherein the compound is S-methyl-L-thiocitrulline or a physiologically acceptable acid addition salt thereof.

17. The method of claim 15 wherein the compound is S-methyl-L-homothiocitrulline or a physiologically acceptable acid addition salt thereof.

* * * * *